(12) United States Patent
Dixit et al.

(10) Patent No.: US 9,006,443 B2
(45) Date of Patent: *Apr. 14, 2015

(54) PROCESS FOR PREPARING QUINOLINE-3-CARBOXAMIDE DERIVATIVES

(71) Applicant: Actavis Group PTC ehf, Hafnarfjorour (IS)

(72) Inventors: Girish Dixit, Uttar Pradesh (IN); Krishnadatt Sharma, Maharashtra (IN); Kundan Singh Shekhawat, Rajasthan (IN); Nitin Sharadchandra Pradhan, Maharashtra (IN); Jon Valgeirsson, Hafnarfjordur (IS)

(73) Assignee: Actavis Group PTC ehf (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/020,941

(22) Filed: Sep. 9, 2013

(65) Prior Publication Data

US 2014/0005401 A1    Jan. 2, 2014

Related U.S. Application Data

(63) Continuation of application No. 12/989,796, filed as application No. PCT/IB2009/005780 on Apr. 27, 2009, now Pat. No. 8,552,194.

(30) Foreign Application Priority Data

Apr. 28, 2008  (IN) .......................... 1041/CHE/2008

(51) Int. Cl.
 *C07D 215/56*   (2006.01)
 *C07D 215/22*   (2006.01)
 *A61K 31/4704*  (2006.01)

(52) U.S. Cl.
 CPC ........... *C07D 215/56* (2013.01); *A61K 31/4704* (2013.01); *C07D 215/22* (2013.01)

(58) Field of Classification Search
 CPC .......................... A61K 31/4704; C07D 215/12
 USPC ................................................... 546/155, 90
 See application file for complete search history.

(56) References Cited

U.S. PATENT DOCUMENTS

| 4,547,511 A | 10/1985 | Eriksoo et al. |
| 6,077,851 A | 6/2000 | Bjork et al. |
| 6,875,869 B2 | 4/2005 | Jansson |
| 8,552,194 B2 * | 10/2013 | Dixit et al. ................... 546/155 |
| 2004/0034227 A1 | 2/2004 | Jansson |

OTHER PUBLICATIONS

International Preliminary Report on Patentability; International Application No. PCT/IB2009/005780; International Filing Date Apr. 27, 2009; Date of Mailing Nov. 11, 2010; Agent's File Reference ADC0016PCT; 8 pages.
Jonsson, J Med Chem, "Sythesis and Biological Evaluation of New 1,2-Dihydro-4-hydroxy-2-oxo-3-quinolinecarboxamides for Treatment of Autoimmune Disorders: Structure-Activity Relationship"; vol. 47, 2075-2088, 2004.
International Search Report and Written Opinion; International Application No. PCT/IB2009/005780; International Filing Date Apr. 27, 2009; Date of Mailing Sep. 1, 2009; 13 pages.
Shi, et al.; "Structure-Activity Relationships Studies of the Anti-Angiogenic Activities of Linomide"; Bioorg & Med Chem Lett, vol. 13, pp. 1187-1189, 2003.
Sjovall, et al.; "Using DOE to Achieve Reliable Drug Administration: A Case Study"; Org Process Res & Dev, vol. 8, pp. 802-807, 2004.
Tojo, et al.; "Quinoline-3-carbothioamides and Related Compounds as Novel Immunomodulating Agents"; Bioorg & Med CHem Lett, vol. 12, pp. 2427-2430, 2002.
Wennerberg, et al.; "Development of a Practical and Reliable Synthesis of Laquinimod"; Org Process Res & Dev, vol. 11, pp. 674-680, 2007.

* cited by examiner

*Primary Examiner* — D M Seaman
(74) *Attorney, Agent, or Firm* — Cantor Colburn LLP

(57) ABSTRACT

Disclosed herein is an improved, commercially viable and industrially advantageous process for the preparation of quinoline-3-carboxamide derivatives such as laquinimod, or a pharmaceutically acceptable salt thereof, in high yield and purity.

20 Claims, No Drawings

PROCESS FOR PREPARING QUINOLINE-3-CARBOXAMIDE DERIVATIVES

CROSS REFERENCE TO RELATED APPLICATION

This application is a continuation of U.S. application Ser. No. 12/989,796, filed Dec. 30, 2010, which is a 371 of PCT/IB2009/005780 filed Apr. 27, 2009, which claims the benefit of priority to Indian provisional application No. 1041/CHE/2008, filed on filed on Apr. 28, 2008, under the provisions of 35 U.S.C. 119 and the International Convention for the protection of Industrial Property, which are incorporated herein by reference in their entirety.

FIELD OF THE DISCLOSURE

Disclosed herein is an improved, commercially viable and industrially advantageous process for the preparation of quinoline-3-carboxamide derivatives such as laquinimod, or a pharmaceutically acceptable salt thereof, in high yield and purity.

BACKGROUND

U.S. Pat. No. 6,077,851 discloses a variety of quinoline-3-carboxamide derivatives and their salts, processes for their preparation, pharmaceutical compositions comprising the derivatives, and method of use thereof. These compounds are useful for clinical treatment of diseases resulting from autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. Of these compounds, N-ethyl-N-phenyl-1,2-dihydro-4-hydroxy-5-chloro-1-methyl-2-oxoquinoline-3-carboxamide is important, since it is well-known as a pharmaceutically active substance under the name of Laquinimod. Laquinimod is a promising immunomodulatory agent and useful for the treatment of multiple sclerosis and its manifestations. Laquinimod is represented by the following structural formula I(i):

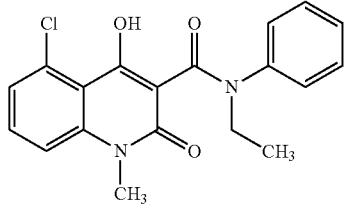

I(i)

Processes for the preparation of laquinimod and its sodium salt are disclosed in U.S. Pat. Nos. 6,077,851 and 6,875,869.

U.S. Pat. No. 6,077,851 (hereinafter referred to as the '851 patent) describes several synthetic routes for preparing laquinimod. According to first synthetic process, laquinimod is prepared by the reaction of 1,2-dihydro-4-hydroxy-5-chloro-1-methyl-2-oxo-quinoline-3-carboxylic acid ethyl ester with N-ethylaniline in a suitable solvent such as toluene, xylene and the like, to produce a reaction mass containing laquinimod, followed by distillation of ethanol formed during the reaction and then subjected to usual work up to produce laquinimod, which is then converted into its sodium salt.

According to a second synthetic process as described in the '851 patent, laquinimod is prepared by the reaction of 5-chloro isatoic anhydride with N-ethyl-N-phenylcarbamoyl acetic acid ethyl ester in the presence of methyl iodide and a strong base such as sodium hydride in a suitable solvent such as N,N-dimethylacetamide.

According to a third synthetic process as described in the '851 patent, laquinimod is prepared by the reaction of 1,2-dihydro-4-hydroxy-5-chloro-1-methyl-2-oxo-quinoline-3-carboxylic acid with N-ethylaniline using coupling reagents such as carbodiimides and thionyl chloride in the presence of triethylamine to produce laquinimod.

Laquinimod obtained by the processes described in the '851 patent does not have satisfactory purity. Unacceptable amounts of impurities are generally formed along with laquinimod, thus resulting in low yields of the product. Moreover, the processes involve the use of additional, explosive and hazardous reagents like sodium hydride, methyl iodide and thionyl chloride. The use of thionyl chloride and sodium hydride is not advisable for scale up operations.

U.S. Pat. No. 6,875,869 (hereinafter referred to as the '869 patent) describes an improved process for the preparation of laquinimod comprising reacting 1,2-dihydro-4-hydroxy-5-chloro-1-methyl-2-oxo-quinoline-3-carboxylic acid methyl ester with N-ethylaniline in the presence of a solvent selected from straight or branched alkanes and cycloalkanes or mixtures thereof with a boiling point between 80° C. and 200° C., specifically n-heptane, n-octane or mixtures thereof. This process has the disadvantage that the preparation of laquinimod takes place essentially at higher temperatures using high boiling point solvents, and these solvents furthermore also have to be used in high volumes, for example, about 20 volumes, with respect to the methyl ester intermediate.

Based on the aforementioned drawbacks, the prior art processes may be unsuitable for preparation of laquinimod in commercial scale operations.

A need remains for an improved and commercially viable process of preparing a substantially pure laquinimod, derivatives thereof, or a pharmaceutically acceptable salt thereof to resolve the problems associated with the processes described in the prior art, and that will be suitable for large-scale preparation. Desirable process properties include less hazardous and environmentally friendly reagents, lesser reaction time, reduced cost, and greater simplicity, increased purity and increased yield of the product.

SUMMARY

The present inventors have surprisingly and unexpectedly found that quinoline-3-carboxamide derivatives such as laquinimod can be prepared in high purity and with high yield by reacting substituted 1-methyl-2-oxo-quinoline-3-carboxylic acid with N-alkylaniline in the presence of a suitable coupling reagent such as dichlorotriphenyl phosphorane, optionally in the presence of a suitable base, in a suitable solvent. The novel process solves the drawbacks associated with the prior processes and is commercially viable for preparing quinoline-3-carboxamide derivatives.

In one aspect, the present invention provides an efficient, convenient, commercially viable and environment friendly process for the preparation of laquinimod, derivatives thereof, or a pharmaceutically acceptable salt thereof. Moreover, the process disclosed herein can be advantageously carried out, in short reaction times, at low temperatures using low boiling point solvents such as methylene chloride in low volumes. Advantageously, the reagents used for the present invention are less hazardous and easy to handle at commercial scale and also involves less expensive reagents.

DETAILED DESCRIPTION

According to one aspect, there is provided an improved process for the preparation of a substituted quinoline-3-carboxamide compound of formula I:

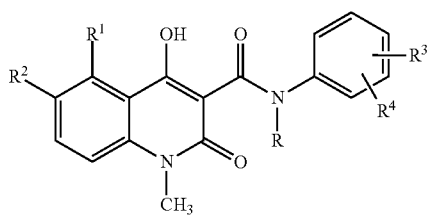

wherein

R is selected from methyl, ethyl, n-propyl, iso-propyl, n-butyl, iso-butyl, sec.-butyl and allyl;

$R^1$ is selected from methyl, ethyl, n-propyl, iso-propyl, methoxy, ethoxy, methylthio, ethylthio, n-propylthio, methylsulphinyl, ethylsulphinyl, fluoro, chloro, bromo, trifluoromethyl, difluoromethoxy and trifluoromethoxy;

$R^2$ is hydrogen; or $R^1$ and $R^2$ together can be methylenedioxy, ethylenedioxy and isopropylidenedioxy;

$R^3$ is selected from hydrogen, methyl, ethyl, n-propyl, iso-propyl, methoxy, ethoxy, fluoro, chloro, bromo, trifluoromethyl, difluoromethoxy and trifluoromethoxy; and $R^4$ is selected from hydrogen, fluoro and chloro, with the proviso that $R^4$ is selected from fluoro and chloro only when $R^3$ is selected from fluoro and chloro;

which comprises:

reacting a quinoline-3-carboxylic acid derivative of formula II:

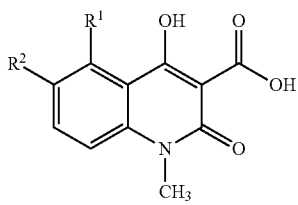

wherein $R^1$ and $R^2$ are as defined in formula I;

with an aniline derivative of formula III:

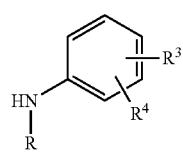

wherein R, $R^3$ and $R^4$ are as defined in formula I;

in the presence of a suitable coupling agent in a suitable solvent to provide a substantially pure compound of formula I and optionally converting the compound of formula I obtained into a pharmaceutically acceptable salt thereof;

wherein the coupling agent is selected from the group consisting of dichlorotriphenyl phosphorane, phosphorous oxychloride, O-benzotriazole-N,N,N',N'-tetramethyl-uronium-hexafluoro-phosphate (HBTU), and combinations comprising one or more of the foregoing coupling agents. A specific coupling agent is dichlorotriphenyl phosphorane.

In one embodiment, the compounds of formulae I and II wherein $R^1$ is chloro; and $R^2$ is hydrogen. In another embodiment, the compounds of formulae I and III wherein R is ethyl; $R^3$ and $R^4$ are hydrogen.

Exemplary solvents used herein include, but are not limited to, a chlorinated hydrocarbon, a hydrocarbon, a ketone, an ester, an ether, a nitrile, a polar aprotic solvent, and mixtures thereof. The term solvent also includes mixtures of solvents.

In one embodiment, the solvent is selected from the group consisting of methylene chloride, ethylene dichloride, chloroform, carbon tetrachloride, n-pentane, n-hexane, n-heptane, cyclohexane, toluene, xylene, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, tetrahydrofuran, dioxane, diethyl ether, diisopropyl ether, monoglyme, diglyme, N,N-dimethylformamide, N,N-dimethylacetamide, dimethylsulfoxide, and mixtures thereof.

Specifically, the solvent is a chlorinated hydrocarbon solvent selected from the group consisting of methylene chloride, ethylene dichloride, chloroform, carbon tetrachloride, and mixtures thereof; and a more specific solvent is methylene chloride.

In one embodiment, the amount of chlorinated hydrocarbon solvent employed in the coupling reaction can range from about 5 volumes to about 15 volumes and specifically from about 7 volumes to about 10 volumes with respect to the quinoline-3-carboxylic acid derivative of formula II.

The reaction temperature and time period for coupling the compounds of Formulae II and III will ordinarily depend on the starting compounds, the coupling agent, the base and the solvent employed in the reaction. The reaction is specifically carried out at a temperature of about 0° C. to the reflux temperature of the solvent used for at least 20 minutes, more specifically at a temperature of about 25° C. to the reflux temperature of the solvent used for about 30 minutes to about 10 hours, and most specifically at the reflux temperature of the solvent used for about 1 hour to about 5 hours. The reaction is advantageously conducted under an inert atmosphere such as nitrogen.

As used herein, "reflux temperature" means the temperature at which the solvent or solvent system refluxes or boils at atmospheric pressure.

In one embodiment, a specific compound of formula I prepared by the process described herein is laquinimod of formula I(i) or a salt thereof (formula I, wherein R is ethyl; $R^1$ is chloro; and $R^2$, $R^3$ and $R^4$ are hydrogen):

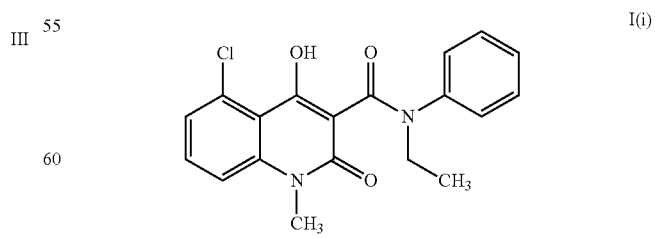

In another embodiment, the reaction is carried out in the presence or absence of a base. The base is an organic or inorganic base. Specific organic bases are tributylamine, triethylamine, diisopropylethylamine, diethylamine, tert-butyl amine, pyridine, N-methylmorpholine and 4-(N,N-dimethylamino)pyridine.

In another embodiment, the base is an inorganic base. Exemplary inorganic bases include, but are not limited to, a hydroxide, a carbonate, an alkoxide and a bicarbonate of alkali or alkaline earth metals. Specific inorganic bases are sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide, and more specifically sodium hydroxide, potassium hydroxide, sodium carbonate and potassium carbonate.

In one embodiment, the coupling agent is used in a molar ratio of about 1 to about 6 moles, specifically about 2 to about 4 moles, per 1 mole of the quinoline-3-carboxylic acid derivative of formula II in order to ensure a proper course of the reaction.

The coupling reagents employed for the coupling reaction disclosed herein allows the product to be easily isolated and purified, thereby producing a product with 90-95% overall yield.

The reaction mass containing the substituted quinoline-3-carboxamide compound of formula I obtained may be subjected to usual work up such as a washing, an extraction, an evaporation, a pH adjustment etc., followed by isolation as solid from a suitable solvent by conventional methods such as cooling, seeding, partial removal of the solvent from the solution, by adding an anti-solvent to the solution, evaporation, vacuum drying, spray drying, freeze drying, or a combination thereof.

The solvent used for isolating the pure substituted quinoline-3-carboxamide compound of formula I is selected from the group consisting of water, acetone, methanol, ethanol, n-propanol, isopropanol, ethyl acetate, methylene chloride, n-pentane, n-hexane, n-heptane, cyclohexane, toluene, and mixtures thereof. More specifically, the solvent is a mixture of water and ethyl acetate.

In one embodiment, the isolation is carried out by cooling the solution at a temperature of below 30° C. for at least 30 minutes, specifically at about 0° C. to about 30° C. for about 1 hour to about 20 hours, and more specifically at about 0° C. to about 25° C. for about 2 hours to about 10 hours. The solid obtained is collected by filtration, filtration under vacuum, decantation, centrifugation, filtration employing a filtration media of a silica gel or celite, or a combination thereof.

The substituted quinoline-3-carboxamide compound of formula I obtained by the process disclosed herein may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 70° C. The drying can be carried out for any desired time period that achieves the desired result, such as about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer and the like. Drying equipment selection is well within the ordinary skill in the art.

The substituted quinoline-3-carboxamide compound of formula I, specifically laquinimod of formula I(i) (wherein R is ethyl; $R^1$ is chloro; and $R^2$, $R^3$ and $R^4$ are hydrogen), obtained by the process disclosed herein, have a purity (measured by High Performance Liquid Chromatography, hereinafter referred to as 'HPLC') greater than about 98%, specifically greater than about 99%, more specifically greater than about 99.5%, and still more specifically greater than about 99.9%. For example, the purity of the laquinimod of formula I(i) can be about 99% to about 99.95%, or about 99.5% to about 99.99%.

The use of inexpensive, non-explosive, non-hazardous, readily available and easy to handle reagents allows the process disclosed herein to be suitable for preparation of laquinimod at lab scale and in commercial scale operations.

Pharmaceutically acceptable salts of the substituted quinoline-3-carboxamide compound of formula I can be prepared in high purity by using the substantially pure compounds of formula I obtained by the methods disclosed herein, by known methods, for example as described in U.S. Pat. No. 6,077,851.

Pharmaceutically acceptable salts of the compounds of formula I can be obtained from alkali or alkaline earth metals including sodium, calcium, potassium and magnesium, and more specifically sodium.

The present inventors have further surprisingly found that the yield and purities of laquinimod are increased when diisopropylethylamine or pyridine is used as a base instead of triethylamine in the reaction between 1,2-dihydro-4-hydroxy-5-chloro-1-methyl-2-oxo-quinoline-3-carboxylic acid and N-ethyl aniline in the presence of thionyl chloride.

According to another aspect, there is provided an improved process for the preparation of laquinimod of formula I(i) or a pharmaceutically acceptable salt thereof, comprising reacting 1,2-dihydro-4-hydroxy-5-chloro-1-methyl-2-oxo-quinoline-3-carboxylic acid with N-ethyl aniline in the presence of thionyl chloride and a base selected from the group consisting of diisopropylethylamine and pyridine; and isolating pure laquinimod from a suitable solvent and optionally converting the laquinimod obtained into its pharmaceutically acceptable salts thereof.

In one embodiment, the reaction is carried out in the presence of a solvent. Exemplary solvent used herein includes, but are not limited to, a chlorinated hydrocarbon, a hydrocarbon, a ketone, an ester, an ether, a nitrile, a polar aprotic solvent, and mixtures thereof. The term solvent also includes mixtures of solvents.

In another embodiment, the solvent is selected from the group consisting of methylene chloride, ethylene dichloride, chloroform, carbon tetrachloride, n-pentane, n-hexane, n-heptane, cyclohexane, toluene, xylene, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, tetrahydrofuran, dioxane, diethyl ether, diisopropyl ether, monoglyme, diglyme, N,N-dimethylformamide, N,N-dimethylacetamide, dimethylsulfoxide, and mixtures thereof. Specifically, the solvent is selected from the group consisting of methylene chloride, ethylene dichloride, chloroform, n-pentane, n-hexane, n-heptane, cyclohexane, toluene, xylene, and mixtures thereof; and more specifically methylene chloride and toluene.

The reaction is carried out at a temperature of about 0° C. to the reflux temperature of the solvent used for at least 20 minutes, specifically at a temperature of about 25° C. to the reflux temperature of the solvent used for about 1 hour to about 20 hours, and most specifically at the reflux temperature of the solvent used for about 3 hours to about 7 hours. In one embodiment, the base is used in a molar ratio of about 1.5 to about 5 moles, specifically about 2 to about 3.5 moles, per 1 mole of 1,2-dihydro-4-hydroxy-5-chloro-1-methyl-2-oxo-quinoline-3-carboxylic acid.

In another embodiment, the thionyl chloride is used in a molar ratio of about 1 to about 3 moles, specifically about 1 to about 2 moles, per 1 mole of 1,2-dihydro-4-hydroxy-5-chloro-1-methyl-2-oxo-quinoline-3-carboxylic acid.

The diisopropylethylamine or pyridine is used as a base for the coupling reaction, allows the product to be easily isolated and purified, thereby producing a product with 80-90% overall yield.

The reaction mass containing laquinimod obtained may be subjected to usual work up such as a washing, an extraction, an evaporation, a pH adjustment etc., followed by isolating as a solid by the methods described herein above.

Laquinimod obtained by the process disclosed herein, has a purity of greater than about 97%, specifically greater than about 98%, and more specifically greater than about 99% as measured by HPLC.

The following examples are given for the purpose of illustrating the present disclosure and should not be considered as limitation on the scope or spirit of the disclosure.

Comparative Example

Preparation of Laquinimod According to the Method Described in the U.S. Pat. No. 6,077,851

The mixture of 1,2-dihydro-4-hydroxy-5-chloro-1-methyl-2-oxo-quinoline-3-carboxylic acid (1 gm) and methylene chloride (20 ml) was cooled to 5-10° C. under nitrogen atmosphere. Triethylamine (1.15 gm) was added to the resulting mass at 5-10° C. to form a clear solution. The solution was followed by addition of N-ethyl aniline (0.45 gm) in one portion at 5-10° C. and then thionyl chloride (0.48 gm) was added at 5-10° C. The resulting mixture was stirred for 4 hours followed by evaporation of methylene chloride under vacuum. The resulting residue was dissolved in ethyl acetate (100 ml) followed by washings with 5% sodium hydroxide solution (30 ml) at 25-30° C. The resulting aqueous layer was cooled to 10-15° C. and pH was adjusted to 2 by using 18% aqueous hydrochloric acid solution (20 ml). The resulting mass was stirred for 2 hours at 15-20° C. The resulting white colored solid was filtered and dried at 55-60° C. to yield 0.73 gm of laquinimod (HPLC Purity: 84.31%).

EXAMPLES

Example 1

Preparation of N-Ethyl-N-phenyl-1,2-dihydro-4-hydroxy-5-chloro-1-methyl-2-oxoquinoline-3-carboxamide (Laquinimod)

N-Ethyl aniline (5.2 gm) was taken in methylene chloride (100 ml) and stirred for 10 minutes at 25-30° C. under nitrogen atmosphere. The resulting mass was followed by the addition of dichlorotriphenyl phosphorane (26.6 gm) at 25-30° C. and the reaction mixture was stirred for 15 minutes. 1,2-Dihydro-4-hydroxy-5-chloro-1-methyl-2-oxo-quinoline-3-carboxylic acid (10 gm) was added to the resulting mass at 25-30° C. followed by heating to reflux (40-45° C.) and then stirred for 3 hours at reflux. Methylene chloride was distilled out from the reaction mass under vacuum at below 45° C. The resulting residue was cooled to 25-30° C., followed by the addition of ethyl acetate (50 ml) and water (50 ml) at 25-30° C. and the resulting mixture was stirred for 30 minutes at 25-30° C. The separated solid was filtered, washed with water and then dried to yield 11.7 gm of laquinimod as a white colored solid (HPLC purity: 99.47%).

Example 2

Preparation of N-Ethyl-N-phenyl-1,2-dihydro-4-hydroxy-5-chloro-1-methyl-2-oxoquinoline-3-carboxamide (Laquinimod)

N-Ethyl aniline (5.2 gm) was taken in chloroform (100 ml) and stirred for 10 minutes at 25-30° C. under nitrogen atmosphere. The resulting mass was followed by the addition of dichlorotriphenyl phosphorane (26.6 gm) at 25-30° C. and the reaction mixture was stirred for 15 minutes. 1,2-Dihydro-4-hydroxy-5-chloro-1-methyl-2-oxo-quinoline-3-carboxylic acid (10 gm) was added to the resulting mass at 25-30° C. followed by heating to reflux (40-45° C.) and then stirred for 3 hours at reflux. Chloroform was distilled out from the reaction mass under vacuum at below 55° C. The resulting residue was cooled to 25-30° C., followed by the addition of ethyl acetate (50 ml) and water (50 ml) at 25-30° C. and the resulting mixture was stirred for 30 minutes at 25-30° C. The separated solid was filtered, washed with water and then dried to yield 12.95 gm of laquinimod (HPLC purity: 99.24%).

Example 3

Preparation of N-Ethyl-N-phenyl-1,2-dihydro-4-hydroxy-5-chloro-1-methyl-2-oxoquinoline-3-carboxamide (Laquinimod)

1,2-Dihydro-4-hydroxy-5-chloro-1-methyl-2-oxo-quinoline-3-carboxylic acid (2 gm) and N-ethyl aniline (1 gm) were taken in toluene (50 ml) and stirred for 30 minutes at 25-30° C. under nitrogen atmosphere. The resulting mass was followed by the addition of dichlorotriphenyl phosphorane (10.5 gm) at 25-30° C., followed by heating to reflux (110-115° C.) and then maintained for 3 hours at reflux. Toluene was distilled out from the reaction mass under vacuum at below 60° C. The resulting residue was dissolved in ethyl acetate (100 ml) at 25-30° C. followed by the addition of water (100 ml) at 25-30° C. and then pH of the resulting mass was adjusted to 10-12 with 10% sodium hydroxide solution at 25-30° C. The resulting mass was stirred for 30 minutes at 20-25° C. followed by separation of the layers. The resulting aqueous layer was cooled to 15-20° C. and pH was adjusted to 2 by using concentrated hydrochloric acid. The resulting mass was stirred for 30 minutes at 15-20° C. The separated solid was filtered, washed with water and then dried to yield 2 gm of laquinimod (HPLC purity: 98.4%).

Example 4

Preparation of N-Ethyl-N-phenyl-1,2-dihydro-4-hydroxy-5-chloro-1-methyl-2-oxoquinoline-3-carboxamide (Laquinimod)

The mixture of 1,2-dihydro-4-hydroxy-5-chloro-1-methyl-2-oxo-quinoline-3-carboxylic acid (15 gm) and methylene chloride (105 ml) was cooled to 5-10° C. under nitrogen atmosphere. Diisopropylethyl amine (26.7 gm) was added to the resulting mass for 5 minutes at 5-10° C. to form a clear solution. The solution was followed by the addition of N-ethyl aniline (7.8 gm) in one portion at 5-10° C. and then thionyl chloride (9.1 gm) was added at 5-10° C. The resulting mixture was stirred for 7 hours followed by evaporation of methylene chloride under vacuum. The resulting residue was dissolved in ethyl acetate (200 ml) followed by washings with 5% sodium hydroxide solution (65 ml) at 25-30° C. The resulting aqueous layer was cooled to 10-15° C. followed by adjusting pH of the mass to 1 by using 18% aqueous hydrochloric acid solution (25 ml). The resulting mass was stirred for 1 hour at 10-15° C. The separated white colored solid was filtered and dried at 55-60° C. to yield 19.3 gm of laquinimod (HPLC Purity: 98.41%).

Example 5

Preparation of N-Ethyl-N-phenyl-1,2-dihydro-4-hydroxy-5-chloro-1-methyl-2-oxoquinoline-3-carboxamide (Laquinimod)

The mixture of 1,2-dihydro-4-hydroxy-5-chloro-1-methyl-2-oxo-quinoline-3-carboxylic acid (1 gm) and toluene (50 ml) was cooled to 10-15° C. under nitrogen atmosphere. Diisopropylethyl amine (1.78 gm) was added to the resulting mass at 10-15° C. to form a clear solution. The solution was followed by the addition of N-ethyl aniline (0.52 gm) in one portion at 10-15° C. and then thionyl chloride (0.61 gm) was added at 0° C. The resulting mixture was stirred for 4 hours and toluene was distilled out under vacuum at below 60° C. The resulting residue was dissolved in ethyl acetate (50 ml) and washed with 5% sodium hydroxide solution (6.5 ml) at 25-30° C. The resulting aqueous layer was cooled to 10-15° C. followed by adjusting pH of the mass to 1 by using 18% aqueous hydrochloric acid solution (2.5 ml). The resulting mass was stirred for 1 hour at 10-15° C. The separated white colored solid was filtered and dried at 55-60° C. to yield 1 gm of laquinimod (HPLC Purity: 98.93%).

Example 6

Preparation of N-Ethyl-N-phenyl-1,2-dihydro-4-hydroxy-5-chloro-1-methyl-2-oxoquinoline-3-carboxamide (Laquinimod)

The mixture of 1,2-dihydro-4-hydroxy-5-chloro-1-methyl-2-oxo-quinoline-3-carboxylic acid (1 gm) and toluene (50 ml) was cooled to 5-10° C. under nitrogen atmosphere. Pyridine (1.09 gm) was added to the resulting mass at 5-10° C. to form a clear solution. The solution was followed by the addition of N-ethyl aniline (0.52 gm) in one portion at 5-10° C. and then thionyl chloride (0.61 gm) was added at 5-10° C. The resulting mixture was stirred for 7 hours followed by evaporation of toluene under vacuum. The resulting residue was dissolved in ethyl acetate (25 ml) followed by washings with 5% sodium hydroxide solution (6.5 ml) at 25-30° C. The resulting aqueous layer was cooled to 10-15° C. followed by adjusting pH of the mass to 1 by using 18% aqueous hydrochloric acid solution (2.5 ml). The resulting mass was stirred for 1 hour at 10-15° C. The separated white colored solid was filtered and dried at 55-60° C. to yield 0.9 gm of laquinimod (HPLC Purity: 97.3%).

Example 7

Preparation of Laquinimod Sodium

Laquinimod (2.7 gm) was taken in ethanol (13 ml) and stirred at 25-30° C. followed by the addition of sodium hydroxide solution (0.33 gm of NaOH in 0.4 ml of water). The resulting solution was stirred for 15 minutes followed by filtration through hyflow bed and washing of the bed with ethanol (7 ml). The resulting clear solution was then stirred for 16 hours at 25-30° C. The separated solid was filtered, washed with chilled ethanol (2 ml) and then dried at 60-65° C. to yield 2.33 gm of laquinimod sodium as a white solid (HPLC Purity: 99.92%).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:
1. A process for the preparation of laquinomod of formula I:

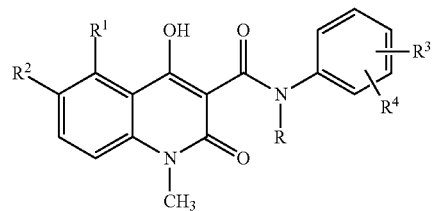

wherein R is ethyl; $R^1$ is chloro; and $R^2$, $R^3$ and $R^4$ are hydrogen
comprising:
reacting a quinoline-3-carboxylic acid derivative of formula II:

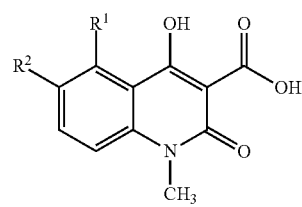

wherein R¹ and R² are as defined in formula I;
with an aniline derivative of formula III:

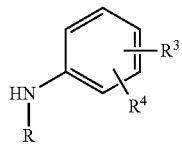

wherein R, R³ and R⁴ are as defined in formula I; in the presence of a coupling agent in a solvent to provide a substantially pure compound of formula I and optionally converting the compound of formula I obtained into a pharmaceutically acceptable salt thereof;

wherein the coupling agent is selected from the group consisting of dichlorotriphenyl phosphorane, phosphorous oxychloride, O-benzotriazole-N,N,N',N'-tetramethyl-uronium-hexafluoro-phosphate (HBTU), and combinations comprising one or more of the foregoing coupling agents.

2. The process of claim 1, wherein the coupling agent is dichlorotriphenyl phosphorane.

3. The process of claim 1, wherein the solvent used in the coupling reaction is selected from the group consisting of a chlorinated hydrocarbon, a hydrocarbon, a ketone, an ester, an ether, a nitrile, a polar aprotic solvent, and mixtures thereof.

4. The process of claim 3, wherein the solvent is selected from the group consisting of methylene chloride, ethylene dichloride, chloroform, carbon tetrachloride, n-pentane, n-hexane, n-heptane, cyclohexane, toluene, xylene, acetone, methyl ethyl ketone, methyl isobutyl ketone, methyl tert-butyl ketone, acetonitrile, ethyl acetate, methyl acetate, isopropyl acetate, tert-butyl methyl acetate, ethyl formate, tetrahydrofuran, dioxane, diethyl ether, diisopropyl ether, monoglyme, diglyme, N,N-dimethylformamide, N,N-dimethylacetamide, dimethylsulfoxide, and mixtures thereof.

5. The process of claim 1, wherein the solvent used in the coupling reaction is a chlorinated hydrocarbon solvent, wherein the chlorinated hydrocarbon solvent is selected from the group consisting of methylene chloride, ethylene dichloride, chloroform, carbon tetrachloride, and mixtures thereof.

6. The process of claim 5, wherein the solvent is methylene chloride or chloroform.

7. The process of claim 1, wherein the reaction is carried out at a temperature of about 0° C. to the reflux temperature of the solvent used for at least 20 minutes.

8. The process of claim 1, wherein the reaction is carried out in the presence or absence of an organic or inorganic base.

9. The process of claim 8, wherein the organic base is selected from the group consisting of tributylamine, triethylamine, diisopropylethylamine, diethylamine, tert-butyl amine, pyridine, N-methylmorpholine and 4-(N,N-dimethylamino)pyridine; and wherein the inorganic base is selected from the group consisting of a hydroxide, a carbonate, an alkoxide and a bicarbonate of alkali or alkaline earth metals.

10. The process of claim 9, wherein the inorganic base is selected from the group consisting of sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide.

11. The process of claim 1, wherein the coupling agent is used in a molar ratio of about 1 to about 6 moles per 1 mole of the quinoline-3-carboxylic acid derivative of formula II.

12. The process of claim 11, wherein the coupling agent is used in a molar ratio of about 2 to about 4 moles per 1 mole of the quinoline-3-carboxylic acid derivative of formula II.

13. The process of claim 1, wherein the reaction mass containing the substituted quinoline-3-carboxamide compound of formula I obtained is subjected to a washing, an extraction, an evaporation and/or pH adjustment; followed by isolating as a solid from a solvent by cooling, seeding, partial removal of the solvent from the solution, by adding an anti-solvent to the solution, evaporation, vacuum drying, spray drying, freeze drying, or a combination thereof.

14. The process of claim 13, wherein the solvent used for isolation is selected from the group consisting of water, acetone, methanol, ethanol, n-propanol, isopropanol, ethyl acetate, methylene chloride, n-pentane, n-hexane, n-heptane, cyclohexane, toluene, and mixtures thereof.

15. The process of claim 1, wherein the laquinomod of formula 1 has a purity of greater than 97%.

16. The process of claim 1, wherein the laquinomod of formula 1 has a purity of greater than 98%.

17. The process of claim 1, wherein the laquinomod of formula 1 has a purity of greater than 99%.

18. Laquinomod produced by the process of claim 1 and having a purity of greater than 97%.

19. The laquinomod of claim 18, having a purity of greater than 98%.

20. The laquinomod of claim 18, having a purity of greater than 99%.

* * * * *